United States Patent

Seguin et al.

[11] Patent Number: 6,046,340
[45] Date of Patent: Apr. 4, 2000

[54] IMIDAZOLE CONTAINING PSEUDODIPEPTIDE PRODUCT AND COMPOSITIONS CONTAINING THE SAME

[75] Inventors: Marie-Christine Seguin, Eze, France; Marc Babizhayev, Moscow, Russian Federation

[73] Assignee: Exsymol Societe Anonyme Monegasque, Monaco

[21] Appl. No.: 08/637,790

[22] PCT Filed: Nov. 3, 1994

[86] PCT No.: PCT/FR94/01272

§ 371 Date: Jul. 18, 1996

§ 102(e) Date: Jul. 18, 1996

[87] PCT Pub. No.: WO95/12581

PCT Pub. Date: May 11, 1995

[30] Foreign Application Priority Data

Nov. 5, 1993 [FR] France .................................. 93 13480

[51] Int. Cl.[7] .......................... C07D 233/64; E12P 17/10; A61K 31/415; A61K 7/42
[52] U.S. Cl. .................... 548/335.5; 424/1.65; 424/94.1; 424/184.1; 424/532; 435/121; 514/397; 514/398; 514/399; 514/400; 548/338.1
[58] Field of Search .............................. 548/338.1, 335.5; 514/397–400; 424/532, 94.1, 1.65, 184.1; 435/121

[56] References Cited

U.S. PATENT DOCUMENTS

| | | | |
|---|---|---|---|
| 2,301,532 | 11/1942 | Fell | 548/338.1 X |
| 2,581,814 | 1/1952 | Plentl | 548/338.1 |
| 4,962,120 | 10/1990 | Bailey et al. | 514/399 |
| 4,996,221 | 2/1991 | Melmon et al. | 514/399 |

FOREIGN PATENT DOCUMENTS

| | | | |
|---|---|---|---|
| 0143746 | 6/1985 | European Pat. Off. | 548/338.1 |
| 0144290 | 6/1985 | European Pat. Off. | 514/399 |
| 0372818 | 6/1990 | European Pat. Off. | 514/399 |
| 94/19325 | 9/1994 | WIPO | 514/399 |

OTHER PUBLICATIONS

Arold et al, Zeitschrift fur Chemie, vol. 9, No. 9, p. 144, 1969.
Modder et al. J. Org. Chem., vol. 56, No. 19, pp. 5606–5610, 1991.

*Primary Examiner*—Floyd D. Higel
*Attorney, Agent, or Firm*—Ostrenlenk, Faber, Gerb & Soffen, LLP

[57] ABSTRACT

Product pseudodipeptide of general formula:

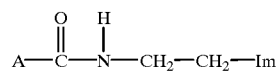

in which A is:
a) under the form:

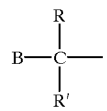

B represent an amine which nitrogen atom which is directly linked to the atom of carbon and chosen among the amines, the imines, the ammoniums, R is an atom of fluorine, a fluoro-alkyl radical, a functional group, an acyl radical, a linear alkyl chain, or an alkenyle or aryl radical, R' is an hydrogen atom, a fluorine atom, an alkyl radical, or fluoro-alkyl radical, and Im is an imidazole or an N-substituted imidazole ring;
b) or the form of

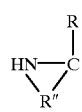

where R is an atom of hydrogen or a fluoro-alkyl or an acyl radical, or an hydrocarbon radical which can be substituted by one or several functional groups, and R" is a hydrocarbon radical or an acyle radical.

20 Claims, No Drawings

IMIDAZOLE CONTAINING PSEUDODIPEPTIDE PRODUCT AND COMPOSITIONS CONTAINING THE SAME

The present invention concerns the pseudodipeptide products, and especially a new pseudodipeptide product possessing an imidazole group or an imidazole N-substituted, as well as applications of such product in the therapeutic, cosmetic and food fields.

The object of the invention is a new pseudodipeptide product having as a general formula:

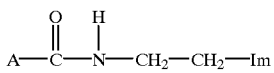

in which
A is:
a) either in the form of

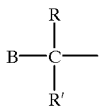

wherein
B represents an amine which nitrogen atom is directly linked to the carbon atom and is choosen from the group consisting of:
1) primary amine
2) secondary amine of formula —NH-X in which X is a hydrocarbon, fluoroalkyl, or acyl radical, or an amine
3) tertiary cyclic amine of cycloalkyl or lactam type
4) tertiary amine of formula

in which Y or Y' is an hydrocarbon, acyl or acyloxy radical,
5) imine of formula

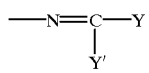

in which Y is an hydrocarbon radical and Y' is an hydrogen atom or an hydrocarbon radical, and
6) ammonium of formula

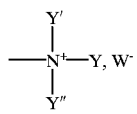

W—
in which Y, Y', Y" is an hydrocarbon radical and the ion W is an halide, sulfate, phosphate, bicarbonate, a para-toluene-sulfonate, or a compound bearing a carboxylic acid group,
R is a fluorine atom, a fluoro-alkyl radical, a functional group such as sulfate, phosphate or carboxylic acid, an acyl radical, a linear alkyl chain that can be substituted by one or several functional groups, alkenyl or aryl radicals that can be substituted by one or several functional groups.
R' is an hydrogen atom, a fluorine atom, an alkyl radical, or a fluoro-alkyl radical,
Im is an imidazole or an N-substituted imidazole such as

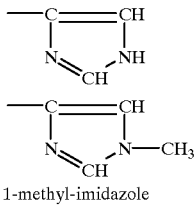

1-methyl-imidazole

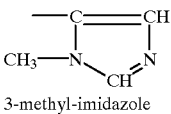

3-methyl-imidazole

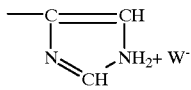

With W as above defined
b) or in the form

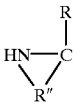

wherein
R is an atom of hydrogen or fluorine, or a fluoro-alkyl or an acyl radical, or an hydrocarbon radical that can be subtituted by one or several functional groups and
R" is an acyl radical or an hydrocarbon radical that can be substituted by one or several functional groups.

In the case in which the general formula of the pseudodipeptide product is of the form a) with B being a lactam more particularly δ- or γ-lactam, or cyclic tertiary amine which can be advantageously

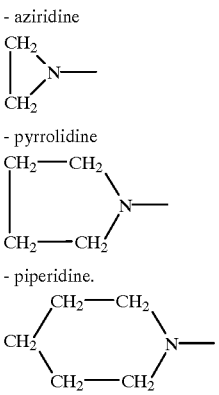

In the case in which the general formula of the pseudodipeptide product is of the form a) being an ammonium, or when the imidazole ring involves an additionnal hydrogen atom on the nitrogen atom, the ion W can be an halide, sulfate, phosphate, bicarbonate, a para-toluene-sulfonate group, a compound bearing a carboxylic acid group such as an acetate, a trifluoracetate, a citrate, a gluconate, a picrate, or an amino acid such as aspartate or glutamate.

In the case in which the general formula of the pseudodipeptide product is of the form a) or b) with R, R' or R"

being an hydrocarbon radical, this latter can be substituted by one or several functional groups such as alcohol, amine, carboxylic acid, alkoxy, thiolether, thiol, phosphate or sulphate.

Some elements of this compound family are capable of forming stable complexes with atoms belonging to the family of transition metals, the "chelates" consisting of an association of metal atom such as zinc, copper, iron, cobalt, manganese, or nickel, zinc being preferably choosen, with one or several pseudodipeptide molecules, this depending on the preparation mode and on the pseudodipeptide kind.

Examples of pseudodipeptide products especially representative of the invention are quoted here-below:

Products corresponding to the general formula having the form a) are:

L-Glutamyl-histamine
 R'=H
 R=CH$_2$—CH$_2$—COOH
 B=NH$_2$
D-Glutamyl-histamine, which is the eniantomer of the previous product
 R'=CH$_2$—CH$_2$—COOH
 R=H
 B=NH$_2$
N-Methyl-2-amino-L-butyryl- histamine
 R'=H
 R=CH$_2$—CH$_3$
 X=CH$_3$
2-aminoisobutyryl-histamine
 R=R'=CH$_3$
 B=NH$_2$
L-norleucyl-histamine
 R'=H
 R=CH$_2$—CH$_2$—CH$_2$—CH$_3$
 B=NH$_2$
L-2-aminooctyl-histamine
 R'=H
 R=CH$_2$—CH$_2$—CH$_2$—CH$_2$—CH$_2$—CH$_3$
 B=NH$_2$
Boc-2-amino-L-pentyl-histamine
 R'=H
 R=CH$_2$—CH$_2$—CH$_3$
 B=tert-Butyl—O—C=O
L-Phenylglicyl-histamine
 R'=H
 R=Phenyl
 B=NH$_2$
L-ornithyl-histamine
 R'=H
 R=CH$_2$—CH$_2$—CH$_2$—NH$_2$
 B=NH$_2$
L-2,6-Diaminopimelyl-histamine
 R'=H
 R=

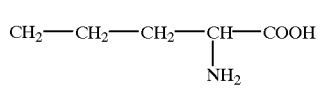

B=NH$_2$
N-acetyl-2-aminobutyryl-histamine
 R'=H
 R=CH$_2$—CH$_3$

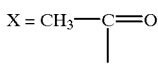

N-phenacetyl-2-aminobutyryl-histamine
 R'=H
 R=CH$_2$—CH$_3$

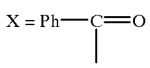

L-Arginyl-histamine
 R'=H
 R=

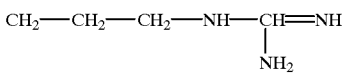

Products corresponding to the general formula having the form b) are
L-prolyl-histamine
 R=H
 R''=CH$_2$—CH$_2$—CH$_2$

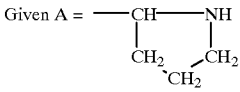

4-hydroxy-L-prolyl-histamine
 R=H
 R''=

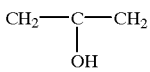

given A=

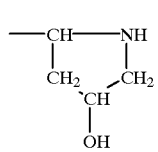

L-pyroglutamyl-histamine

R=H

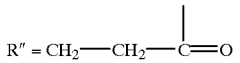

given A =

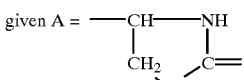

The pseudodipeptide product according to the invention can be considered as a condensation product between an alpha amino acid and the histamine or methyl substituted histamine such as the 1-methyl-histamine or the 3-methyl-histamine. Moreover, we can replace the oxygen atom of the resulting amide bond by a sulphur atom.

For that reason, the pseudodipeptide product can then be obtained by different synthesis processes as well as chemical than enzymatic.

An adequate process of chemical preparation for the preparation of the pseudodipeptide product of the invention indicated, in a symbolic way, with AA-Hist (AA is the amino acid and Hist indicates the histamine) presents itself according to the following scheme

AA+X+Y→X-AA-Y (1)

X-AA-Y+Hist (0.2 HCl)→X-AA-Hist (2)

The first step of the process consists in causing the amino acid (AA) to be N-protected by a group X, and O— activated by a group Y.

The N-protection is preferably carried out by the replacement of an hydrogen atom in the amine of the amino acid which can be an acyl or an acyloxy radical. Among the most interesting protecting groups we can quote the benzyloxycarbonyl (Z), the 9-fluorenyl-methyloxycarbonyl (Fmoc), the benzyl, phthaloyle, 2-nitrophenylsulfenyl and the trifluoroacetyl radicals.

Although it is possible to do without it, the O activation is preferably carried out by esterification of the carboxylic function of the amino acid by a choosen compound in the group consisting of: cyanomethyl alcohol, o-nitrophenol, 2,4,5-trichlorophenol, p-nitrophenol, 2,4-dinitrophenol, pentachlorophenol, pentafluorophenol, N-hydroxyphtalimide, N-hydroxysuccinimide, 1-hydroxypiperidine and 5-chloro-8-hydroxy-quinoline.

Among the modes of O-activation we can again quote the process consisting of transforming the carboxylic acid into an acylchloride, an hydrazide or a "mixed" or symmetrical anhydride.

A particular activation mode consists in getting the amino acid AA to react with phosgene, leading to the formation of the N-carboxyanhydride of this amino acid.

The second step of the preparation process is the coupling with histamine which can be done with or without a coupling agent, by having the N-protected amino acid and O-activated (or not) react with histamine preferably in the dihydrochloride form. It should be stated that the is not essential to use an O-activated amino acid coupling agent.

The coupling without any coupling agent is carried out in an organic solvent (which can be for example, chloroform, 1,2-dimethoxy-ethane, dimethylformamide . . . ) in the presence of an acid (for example acetic acid . . . ) or a base (for example triethylamine) in an hydro-organic solvent (for example water-pyridine, or water-1,2-dimethoxyethane . . . ) with a base (for example soda or sodium bicarbonate . . . ) then acid (for example hydrochloric acid . . . ); in catalytic conditions (for example imidazole, N-ethylmorpholine . . . )

If a coupling agent is used, this agent can be for example the dicyclohexyl-carbodiimide, the N-hydroxybenzotriazole and its derivatves such as the benzotriazolyloxy (trisdimethyl-amino)phosphonium hexafluorophosphate (BOP), the 1-isobutyloxycarbonyl-2-isobutyloxy-1,2-dihydroquinoline, the carbonyldiimidazole, Woodward reagent K, the alpha-chlorovinyl ethyl ether, alpha,alpha-dichlorodiethylether, dichloromethyl methyl ether, DCC and additives, DCC-pentachlorophenol, DCC-pentafluorophoenol, cyanamide, cetenimines and cetenes, oxazolinium salts, EEDQ ('1-ethoxycarbonyl-2-ethoxy-1,2-dihydroquinoleine), ynamines acylphosphoniums, thriphenylphophite and imidazole, copper II complexes, SiCl4.

When it turns out to be necessary the group X or N— protector is eliminated at the time of a third step:

X-AA-Hist→AA-Hist (3)

This elimination is done, according to the protective group, by hydrogenolysis, by reduction with sodium in liquid ammonia, by hydrazinolysis, by acidolysis, by hydrolysis or by an enzymatic way. The favourite solution consists of carrying out this deprotection step by acidolysis with trifluoroacetic acid. In this last case, the pseudodipeptide product is obtained in its base form after treatment by ammonia. Besides, when it is researched, the compound in its base form can be put together with a transition metal salt in order to form a chelate.

As an example, the preparation process of the L-Glutamyl-histamine can be done the following way:

To a suspension of 2.0 g (6.59 mmol) of Boc-Glu-(OtBu)—OH in 1.456 g (7.91 mmol) of pentafluorophenol in solution in 8 ml of ethyl acetate cooled at 0° C., is added drop by drop 4 ml of 1.631 g (7.91 mmol) dicyclohexylcarbodiimide dissolved in ethyl actetate. The shaking at 0° C. is maintained for 30 mn and then during one hour at room temperature.

The reaction mixture is filtered in order to eliminate the dicyclohexyl-urea. The dicyclohexyl-urea is washed with ethyl acetate and the filtrate is evaporated. The oily residue is dried with the paddle pump during 2 hours.

3.1 g of Boc-Glu(OtBu)-Opfp are obtained under the form a a white solid.

To a suspension of 1.213 g (6.59 mmol) of histamine hydrochloride in 15 ml of dimethylformamide containing 1.331 g (13.18 mmol) of N-methyl-morpholine is added at 0° C. drop by drop 5 ml of a solution containing Boc-Glu(OtBu)-OPfp dissolved in dimethylformamide. The reaction mixture is stirred for two hours at 0° C. and then 1 h30 at room temperature. The reaction mixture is filtrated and the precipitate washed with dimethylformamide.

The mixture is filtrated in order to eliminate the precipitate of N-methyl-morpholine chlorhydrate and the precipitate is washed with ethyl acetate, the dimethylformamide is evaporated under vacuum with the paddle pump at t≦40° C. 25 ml of ethyl acetate are added to the residue and then the resulting insoluble fraction is eliminated with filtration.

The product is washed with 20 ml of sodium hydrogenocarbonate 0.5M, 10 ml of sodium hydrogenocarbonate 0.5M, 20 ml of water and 20 ml of a sodium chloride saturated solution.

After drying for one hour the organic phase on sodium sulfate, the evaporation gives a white powder.

3.234 g (yield>100%) of product are recovered but the TLC reveals that some phenol and histamine remain. That will be eliminated during the next step.

To 1.12 g of solid Boc-Glu(OtBu)-Hist is added 25 ml of trifluoroacetic acid. The shaking is maintained for one hour at room temperature. The solvent is evaporated with the paddle pump at t≦40° C.

12 ml of ethyl ether are added to the product which is stirred for 30 minutes at room temperature. A white product is formed while pasting. Ether is decanted, the residue is washed with 10 ml of ethyl ether then dried with the paddle pump.

The residue is then dissolved in 7 ml of ethanol and then ammoniac (5% concentration) is added up to pH 7.5. 25 ml of ethyl acetate are then added and the whole is placed at 0° C. for few hours.

Two phases are formed and they are separated with decantation and the yellowish oily inferior phase is evaporated. A very hygroscopic white powder appears. The product is recrystallized in ethanol/ethyl acetate. After filtration the solid is washed with ethanol/ethyl acetate (1/1).

510 mg of product are obtained (Yield=65%).

The peptoid products can be favourably prepared, in term of yields and cost, using a synthesis method whole or partly enzymatic.

According to this process, we can propose the following synthesis scheme:

The coupling reaction can be described by the following equation:

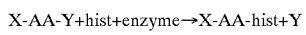

where X-AA-Y is an amino acid N-protected which preparation has already been described and where the protective group X can be an acyl radical, an acyloxy radical . . .

In the present case, the group X enables one also to increase the solubility of AA in the reaction medium. This can lead to the choice of X in order to increase the solubility AA in organic medium such as:

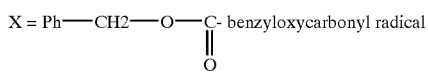

X-AA-Y is O-activated with esterification of the carboxylic function by an alcohol chosen in the group consisting of: aliphatic alcohols, and more especially ethanol, halogenoalkylalcohols such as the 2,2,2-trichloroethanol, aromatic alcohols such as phenol, and all the alcohols previously mentioned for the activation in chemical synthesis. However, this list excludes all tertiary alcohols.

The coupling reaction with histamine (or methylated derivatives) in the base form or with an histamine salt (or one of its methylated derivatives), for example histamine dihydrochloride, can be performed in a range of organic solvents, such as the aliphatic hydrocarbon solvents (cyclohexane, heptane, . . . ) or aromatic (toluene), tertiary alcohols (t-butanol, tert-amylalcohol), the alkyl halides (dichloromethane), ethers (isopropylether), acetonitrile, dimethyformamide or the dimethylsulfoxide.

These solvents can be used alone or in association, anhydrous or in presence of a weak quantity of water.

The reaction can be done in the presence or not of a base, such as triethylamine.

The enzymatic catalyst belongs to the hydrolases family of enzymes (lipase, protease) which can have a microbial, animal or vegetal origin. It can be used in a pure or not purified form.

We can name low cost commercial grades such as lipases, extracted from micro-organisms: Pseudomas sp., *Candida rugosa*, Mucor, or from animal origin: pancreatic lipase of pig (PLP), proteases, trypsine, chymotrypsine, substilisine, papaine, . . .

This catalyst which is not soluble in the reaction medium, is dispersed in the solvent alone or immobilised on an external inert carrier, in order to make easier its recycle.

The reaction is made under a range of temperature included between 4° C. and 70° C., but preferably between 35° C. and 45° C., under stirring.

The coupling product is collected under filtration or after extraction with an appropriated solvent.

Thus, the deprotection and purification steps can be made according the process described for the chemical synthesis.

However, the step of deprotection can be made with an enzymatic reaction according to the reaction:

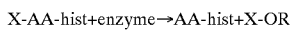

where R=H or an alkyl radical.

The protocol is the same as the one described in the step of coupling, however, we can notice that in the special case where R=H, the reaction is made in water.

For the coupling step, it can be foreseen situations less favourable, but enabling one to reduce the production costs in an important way, using:

an amino acid not N-protected (where X=H), O-activated as previously an N-protected amino acid but not O-activated (where Y=H)

or even the initial amino acid (X=Y=H)

The procedure conditions are the same as the one previously described by the N-protected, O-activated derivatives.

The structural characteristics of the pseudodipeptide product of the invention enable to obtain an active principle not sensitive to the enzymatic deactivation.

The essential structural characteristic is the absence of a carboxylic acid group on the carbon atom located in alpha of the nitrogen of the peptide bound, and for some products of the invention, another structural characteristic is the absence of hydrogen on the carbon atom linked to B (that is to say, R and R' different from H), the hydrogen atom can be replaced by a fluorine atom, a fluoroalkyl radical (R or R'=$CF_3$), or an hydrocarbon radical.

In a general way, the resistance to the enzymatic deactivation is favoured by sterically hindering substitutants present on the terminal carbon (linked to B), such as the isopropyl, isobutyl, sec-butyl, tert-butyl or neopentyl radicals.

The resistance to enzymatic deactivation is also reinforced when the terminal amine is incorporated in a cyclic structure such as the type obtained in b) of the above general formula or of the type obtained in the a) of the general formula where B is a tertiary cyclic amine (e.g. piperidine).

Again in a more general way, the resistance to enzymes, and especially to proteases, is reinforced when the alpha amino acid moiety of the product pseudodipeptide presents a structure which is different from the one of the natural amino acids (thus we can speak about non proteinogenic or non natural amino acids). This can be realised with a judicious choice of the carbon stereochemistry linked to B in the general formula. As a matter of fact, the presence of a terminal asymmetric carbon enables to obtain a different absolute configuration from the one of the natural amino acids.

Pharmacological Properties

The pharmacological properties of the pseudodipeptide product according to the invention comes from this insensitiveness to the enzymatic deactivation.

First of all, they have antioxidative properties. As a matter of fact, they are able to fight against the oxidative stress, that is to say to fight against the damages made by the radical species on the biological structures. These products are able to act at different levels: they are able to react directly on various types of free radicals (F.R.), but also on toxic by-products of the oxidative stress. It is also revealed that these active products can also have a repairing activity towards alterations induced by F.R. on the biological structures.

The reactivity of one of the member of this family compounds towards such or such radical species depends of precise structural elements, without actually being able to establish rules of structure-activity. For instance, it appears that a minor structural difference can leads to an important modification of the pseudodipeptide redox potential, physico-chemical property that is directly linked to the antioxidant potential. This particularity explains the diversity of the properties observed for this family of compounds. For example, the results of in vitro experiments carried out with two pseudodipeptides are presented:

1°) It has been revealed an inhibitory power on the free radical OH.:

Experimental procedure described by J. M. C. Gutteridge in Biochemistry Journal, vol 224 (1984), p. 761–767:
  oxidation substrate: deoxyribose,
  system of production of the hydroxyl radical OH.: EDTA/iron, $H_2O_2$,
  Detection: thiobarbituric acid/mondialdehyde (MDA)
  Antioxidant of reference: dipeptide β-alanyl-L-histidine (sensitive to enzymatic deactivation)

|  | % inhibiton |
| --- | --- |
| Control (without antioxidant) | 0 |
| β-alanyl-L-histidine (10 mM) | 38 |
| L-prolyl-histamine (10 mM) | 62 |
| L-glutamyl-histamine (10 mM) | 0 |

2°) It has been revealed an inhibitory power on the superoxide anion $O_2.-$:

System of production of superoxide anion:xanthine oxydase/hypoxanthine (absence of iron).

The superoxide anion is a reducing substance. It is more especially able to reduce a substrate, the cytochrome C. Its reduction is followed with ultraviolet spectrophotometry to 550 nm.

The percentage of inhibition is described as follows:

$$\frac{\text{Reduction speed of the cytochrome c without inhibitor} - \text{speed reduction with inhibitor}}{\text{Speed reduction of cytochrome c without inhibitor}} \times 100$$

| L-glutamyl-histamine (mM) | % of inhibition |
| --- | --- |
| 1 | 3,5 |
| 5 | 14 |
| 10 | 24 |
| 20 | 35 |

In the enzymatic system which generates superoxide anion, L-glytamyl-histamine is able to strongly inhibit the reduction of the cytochrom c. This inhibition vary according to the concentration. The L-prolyl-histamine, or the antioxidant of reference, the β-alanyl-histamine, do not have the ability to inhibit the superoxyde anion.

In some cases, when B is a secondary amine, the radical X was able to reinforce some antioxidative properties of the pseudodipeptide product according to the invention. This is more especially the case when the substituant X is a tert-butoxycarbonyl or a benzyloxycarbonyl.

Another important property of these products is their ability to protect against the oxidative stress as well as biological lipophilic structures (cell membranes) or hydrophilic (biopymers such as proteins, DNA).

Due to the presence of an imidazole ring and a nucleophile amine, some elements of this family can present an anti-glycation activity and thus oppose themselves to the non enzymatic reaction of sugars on proteins and thus avoid their degradation.

The presence of a moiety structurally similar to histamine enables, for some elements of this family, to obtain an inhibitory activities of the biological effects of histamine.

At the opposite, in some very special cases, it is possible to obtain a compound with a part of the biological properties of histamine.

Finally, theses products present also cytostimulating properties and favour, under a moderate way, the multiplication of certain types of cells. This property can also explain the immunostimulating and immunomodulating behaviour of some members of this family of compounds.

According to this way of action, pseudodipeptides products according to the invention would favour the healing acting on the immune cell system implicated at an advanced stage in the healing (lymphocytes, mastocytes, monocytes) and which main role is the secretion of growth factors.

This "immunostimulating" power is revealed with the help of an in vitro test on murine splenocytes. Then experimental procedure is extracted from: J. Kunert-Radek, H. Stepien, K. Lyson and M. Pawlikowki—"Effects of calcium channel modulators on the proliferation of mouse spleen lymphocytes in vitro"—Agents and Actions, vol. 29 Nos 3–4 (1990), p. 254–258.

The cell proliferation is followed by the measurement of the incorporation rate of the tritiated thymidine in the cells, expressed in number of desintegrations per mn, deduced from the background noise.

The results obtained with an immunostimulator of reference, the concanavaline A, are given for comparison.

The immunostimulating effect is expressed with a stimulation index (SI).

$$IS = \frac{\text{Nb of desintegrations by min of a cell suspension added with a mitogen}}{\text{Nb of desintegrations with mn of a reference cell suspension without mitogen}}$$

The values correspond to the mean value of three measurements.

We can observe a maximal immunostimulating effect for a concentration of 5 µg/ml of L-glutamyl-histamine. To conclude, we observe a moderate immunostimulating effect (cell proliferation) with this pseudodipetide for concentrations ranging between 5 and 10 µg/ml.

|  | Concentration in immunomodulator (µg/ml) | | | |
| --- | --- | --- | --- | --- |
|  | 2.5 | 5.0 | 10.0 | 25.0 |
| IS (L-glutamyl-histamine) | 7.8 | 42.7 | 42.1 | 5.6 |
| IS (concanavaline A) | 8.3 | 33.4 | 61.5 | 4.3 |

This activity is comparable with the one of the reference mitogen:concanavaline A. However, the cell preparation used for this test is heterogenous and actually contains several types of mononucleated cells.

In order to specify the pseudodipeptides mode of action, a second experiment has been carried out on an homogenous population of human monocytes.

Cell proliferation has been evaluated the same way as previously:

|  | Concentration in immunomodulator (µg/ml) | | | |
| --- | --- | --- | --- | --- |
|  | 2.50 | 5.00 | 10.00 | 25.00 |
| IS (L-glutamyl-histamine) | 8.23 | 39.80 | 23.50 | 2.50 |
| IS (concanavaline A) | 4.82 | 29.60 | 21.10 | |

Thus an optimum stimulation of the monocytes is demonstrated for the same concentration than before. We can also observe that this pseudodipeptide is slightly more active than concanavaline A, with an average factor of 1.34.

These results sustain the hypothesis of an indirect mode of action on lymphocytes via the monocytes activation.

In most of the cases, the in vivo preservation of the activity of the pseudodipeptides products of the invention is linked to the preservation of the molecule integrity in contact with hydrolytic enzymatic systems, and especially peptidases.

However, a certain sensitivity of the pseudodipeptides products of the invention towards the enzymatic systems was aimed, for special applications. That is the case where B is a secondary amine with the radical X being:

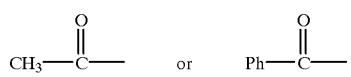

The active product obtained for example in the first case, is capable of being hydrolysed in an in vivo enzymatic way to reform a new pseudodipeptide still active:

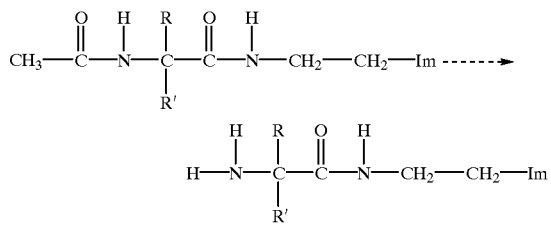

Therefore, we only obtain a temporary protection of the peptoide compound, but it is also a way to reform "in-situ" the primary amine function of the peptoide and thus to re-establish the properties related to the presence in the molecule of a nucleophilic amine, ionisable at physiological pH. We can quote the anti-glycation effect associated partly to an amino compound ability to bound itself by means of a covalent bound on a sugar with reducing propeties.

This strategy can be useful when it is wished: to modify the initial peptoide polarity (in order to make it compatible with a special formulation for example), to avoid the presence on the molecule of a group ionisable at physiological pH, or finally in order to reduce the peptoide reactivity in relation to other chemical species present in a formulation (incompatibility with the presence of an electrophilic compound).

In some cases, this strategy enables also to improve, the bioavailability and pharmacocinetic of this category of active products, resulting in a potentialization of the pharmacological effect.

Therapeutic and Cosmetologic Applications

All the above mentioned properties lead to cosmetologic and therapeutic applications of pseudodipeptides products according to the invention.

The antioxidative properties of the pseudodipeptides according to the invention allow to propose these products for the treatment of pathologies associated with "oxidative stress".

Among these properties, an important therapeutic application is the cataract treatment. The causes of various cataracts are varied. The implicated mechanisms in these pathologies, being of a "senile cataract" type or of a "diabetic cataract" type, are gathered in two categories: the oxidative mechanisms (M. A. Babizhayev, A. I. Deyev, L. F. Lindberg, "Lipid peroxidation as a possible cause of cataract", Mechanisms of Ageing Dev., Vol 44 (1988); P. 69–89), and the mechanisms of reticulation glycation type (T. J. Lyons, G. Silvestri, J. A. Dunn, D. G. Dyer, J. W. Baynes "Role of glycation of lens crystallins in diabetic and non-diabetic senile cataracts", Diabetes Vol. 40, No 8, (1991), P. 1010–1015).

As it has been seen previously, the antioxidative properties of pseudodipeptides resulting in particular from their anti-free radical activity and "peroxidase" like-activity and also to their anti-glycation activity, make the pseudodipeptides according to the invention effective products for treating cataract. The ability of these compounds to have a repairing activity on the alterations induced by the F.R. on biological structures is especially important in the cataract treatment because it results in lens opacities regression.

The pseudodipeptide products according to the invention can set themselves against the oxidative phenomena responsible for the atherosclerosis. In this pathology, the oxidation of a low density lipoproteic particles (LDL) circulating in the blood is responsible for the fragmentation of the proteic part (apoprotein B) as it is for the lipidic fraction of these particles. The fragments formed would induce the appearance of abnormal cell forms (monocytes and macrophages loaded with cholesterol) capable of aggregating on the blood vessels walls and to form the atheromatous plaque.

Morevoer, the pseudodipeptide products, according to the invention would be especially adapted to the treatment of this desease as far as it has been recently demonstrated that glycation phenomena are also implicated in the genesis of the atheromatous plaque (Ref. T. J. Lyons—"Glycation and oxidation—A role in the pathogenesis of Atherosclerosis"—American Journal of Cardiology, vol. 71, No 6 (1993), p. 1326–1331).

Pseudodipeptide products according to the invention can also counteract the cancerogenesis process insofar it has been demonstrated that radical species derived from oxygen are responsible for the cut or the modification of DNA strands, these transformations being able to be the beginning of the evolution of healthy cells to become tumoral cells.

In the same way, antioxidative properties of the pseudodipeptides products according to the invention, allow to indicate these products for the treatment of pathological inflammatory states, and in particular for the treatment of rheumatoid arthritis. As a matter of fact, the synovial liquid deterioration is a characteristic symptom of the inflammatory arthritis type and it was shown that the degradation of one of its essential constituents, hyaluronic acid, was due to an "oxidative stress". More recent studies (Ref. B. Halliwell and J. M. C. Gutteridge—"Chronic inflammation and the auto immune deseases"—Free Radicals in Biology and Medecine—B. Halliwell and J. M. C. Gutteridge Eds—Clarenton Press (1989), Oxford p. 422–438) have also implicated lipids peroxidation phenomenoms involved in this process, and which would explain the benefic action of the products, according to the invention.

The antioxidative properties of the pseudodipeptides products, according to the invention, can also be used in a radiotherapy as an annexe treatment. This radioprotective effect, already known for the β-alanyl-histidine lean on cytostimulating properties of this type of compound, especially with regard to the cells of the marrow bony, which are very sensitive to the radiations used in radiotherapy.

According to recent data, some of the epileptic symptoms could originate from the lesions produced by the oxygenated free radicals on some regions of the brain (Ref. G. R. Jackson, K. Werrbach-Perer, J. R. Perez-Polo—"Role of nerve growth factor in oxidant-antioxidant balance and neuronal injury—II—A conditioning lesion paradigon"—Journal of Neuroscience Research, vol. 25, No. 3 (1990), p. 369–374). The tissues regenerating properties (nervous in this case) of the products of the invention is an important element in this pathology associated with a degeneration of the nervous tissue. These products could also be indicated for the Parkinson desease treatment in which would be involved an "oxidative stress" concerning the brain tissue.

Some vascular diseases and especially endotoxemia, are associated with the overproduction of a radical specie: the nitric oxide radical NO˙. The action of this radical produced by the endothelial cells and the cells of the smooth muscles of the blood vessels, result in a chronic vasodilatation. This state can especially be very harmful during treatments with vasoconstrictors agents. In the cells, an enzyme, the NO-synthase, catalyses the transformation of an aminoacid, the L-arginine, in NO˙. An antioxidant pseudodipeptide according to the invention containing the radical L-arginyl (or a derivative: NG-methyl-L-arginyl) in its structure, would be able to act directly on NO˙, but also on the enzyme responsible for the NO. synthesis, through an inhibition behaviour on enzyme catalysis.

At the skin level, the antioxidative properties of the pseudodipeptides products of the invention can be used in order to neutralize the effects of the oxygenated free radical species generated by the sunlight. That way they will efficently block the photo-allergic reactions (free radical species induce a the skin level the formation of photosensitizing molecules). In connection with an active principle sensitive to the oxidation (e.g.: Chlorpromazine), they will prevent its transformation in a toxic compound.

This principle finds its best application during the treatments of certain skin diseases with photochemiotherapy. As a matter of fact, these treatments rely upon the use of a photosensitizer (e.g.: psoralen), which under radiation brings a beneficial action (interaction with DNA) but which, unfortunately, is accompanied by free radical species formation, responsible for unwanted secondary effects.

The products of the invention can also be indicated in order to counteract the appearance of cutaneous symptoms among persons suffering from porphyrias, because the porphyrins potentiate the damages caused by the F.R.

They can also set themselves against the formation of cutaneous lesions linked to the "oxidative stress" among persons suffering from autoimmune diseases such as Systemic Lupus Erythematosus (SLE).

They also efficiently counteract the consequences of "sunburns": erythema, edema and formation of characteristic cells in the skin.

The antioxidative properties of compounds according to the invention can of course be used for the prevention of cutaneous ageing. As a matter of fact, numerous experimental arguments, analytical and epidemiological support the theory according to which the accumulation of biochemical damages induced by the F.R. could constitute the essential process of ageing. It is in particular clear that the exposition to sun radiations, responsible for the formation of free radical species derived from oxygen, is the cause of premature cutaneous ageing.

Finally, it has been experimentally proved that these compounds can fight other distinctive phenomena of the ageing cutaneous tissue:

Nonenzymatic crosslinking of proteins such as collagen or elastin mediated by sugars (V. M. Monnier—Nonenzymatic glycosylation, the Maillard reaction and the ageing process"—Journal of Gerontology, vol. 45, No 4 (1990) p. B105–111), The formation of lipoproteic complexes:lipofuscins (crosslinking with by-products of the oxidative stress)

It has been demonstrated that the L-arginine was capable of resisting to nonenzymatic crosslinking (this aminoacid can condense on sugars but also on some dicarbonylated by-products of the oxidative stress). Then, a pseudodipeptide according to the invention containing in its structure a L-arginyl radical will be therefore, especially indicated in order to resist against the mechanism of tissue ageing.

Another series of applications are dependent on the cytostimulating properties of pseudodipeptides products according to the invention and, as it has been demonstrated, of their immunostimulating properties. These properties allow to favour the tissue regeneration and the healing, and in a general way, allow to regulate the functions that involve the mediators of the immune response.

That way, they can be used in order to favour the regeneration of disturbed cutaneous connective tissues. They favour the repair of the mucosa after burns or after chemio and radiotherapies According to this principle, these products can also be indicated for the prevention and in the wrinkles treatments.

Cytostimulating and regenerating properties of the pseudodipeptides act with a particular attention towards the muscular tissues where we can find high concentrations of a related natural dipetide: β-alanyl-histidine. Even if the physiological role of this compound is not, at the present time, perfectly established, it is closely linked to the muscular metabolism. So the products of the invention could participate to the improvement of the muscles contractility, and regulate the heart contractions. We can also use this type of properties for the treatment of some muscular degeneration such as myodystrophy of Dushen.

The healing properties of the pseudodipeptide products according to the invention find their application in numerous fields. We can quote the treatment of gastric ulcers, for which a dipeptide product related to carnosine, has given good results.(M. Ito, T. Tanaka and Y. Susuki—Effect of N-(3-aminoproprionyl-L-histidinato zinc (Z-103) on healing and hydrocortisone-induced release of acetic acid ulcers in rats with limited food-intake-time"—Japanese Journal of Pharmacology, vol. 54 (1990), p. 513–521). Besides, the antioxidant and anti inflammatory properties of the invention products are useful for the treatment of this pathology. A zinc chelate according to the invention, is particularly indicated for this application, as previously described.

Healing properties of the pseudodipeptide products according to the invention are also particularly indicated for the treatment of corneal impairs. They can be administered in the postoperative treatment, after for example, a cornea incision for the correction of myopia. They can also, to the best advantage, be used for the pathologies treatment of "dry eye" favouring the healing of cornea hepitelium, but also thanks to a behaviour of "artificial tear": protection of the damaged tissues against the "oxidative stress" (state of health, inflammation, U.V. radiation), incorporation in formulations favouring the the tear film restoration.

Compositions containing pseudodipeptide products of the invention will also be able, thanks to their immunostimulative and regenerating action of the tissues, resist against the retina degeneration phenomena. They will see their effects reinforced owing to the fact that oxidative reactions are involved in this pathology (Ref. R. E. Anderson, L. M. Rapp, R. D. Wiegand—Current Eye Research, vol.3 (1984), p. 223–227).

The immunostimulative properties of these pseudodipeptides products of the invention can be finally turn to the potentiation of vaccines account in replacement of adjuvants which are usually used in order to reinforce the immune response of human being (aluminium salts, extracts from bacterial origin, monophosphoryl A . . . ) for which the side effects are not insignificant. (R K Gupta, E H Relyveld, E B Lindblad, B Bizzini, S Ben-Efraim and C K Gupta "Adjunvants—a balance between toxicity and adjunvancity" Vaccine, Vol. 11, no 3 (1993), p. 293–306).

As it has already been mentioned, some of the pseudodipeptides complying with the general formula above mentionned, can behave as histamine inhibitors. Among these therapeutical applications using this property, we can quote:

An antagonist of histamine could set himself against the platelets aggregation with applications for the peripheral vascular system affections treatment. As a matter of fact, it has been proved that histamine is an intracellular mediator favouring the aggregation of the platelets. (S. P. Saxena, L. J. Brandes, A. B. Becker K. J. Simons, F. S. La Bella and J. M. Gerrard, Science, vol. 243, no 24 (1989), P. 1596–1599). Histamine is also an intracellular mediator implicated in the development and the cell multiplication (J R. Chanda, A. K. Ganguly Cancer Letters, vol. 34 (1987), P. 207). Therefore, an antagonist pseudodipeptide according to the invention could be used in order to regulate the cell multiplication, in particular in the hypertrophic cicatricial tissues (cheloids).

Histamine is also an extracellular mediator intervening in numerous biological processes. Thus an antagonist according to the invention could be implicated for the allergies, inflammation treatments of some cardiac dysfunctions . . . and for all the pathologies where the excess release of histamine is involved.

So, it could be particularly favourable to include the pseudodipeptides products according to the invention in fragrances and deodorants in order to fight against allergic reactions, and in particular anaphylactic choc, induced by some strong odorous compositions.

In an opposite way to the previous case, some elements of this family of compounds can possess some of the properties of histamine ("pro-histaminic" behaviour). An antagonist behaviour of the histamine H2 receptors allow to inhibit the neutrophiles activation and therefore the excess production of free radicals by these cells. (R. Burde, R. Seifert, A. Buschaeur, G. Schultz, "Histamine inhibits activation of human neutrophils and HL-60 leukemic cells via H2-receptors" Naunyn-Shcmiedebergs Arch. of Pharmacology, vol. 340, no 6 (1989), p. 671–678).

This allows to consider the use of such pseudodipeptides for the treatment of some pathologic inflammatory states.

Histamine favours also the multiplication and the cell development (G. Kahlson, E. Rosengren, C. Steinhardt Journal of Physiology, vol. 151 (1960), P. 131). A compound with "pro-histaminic" could then favour the cell regeneration.

A series of applications are related to the ability of some pseudodipeptides products according to the invention, including in their structure an L-prolyl radical (and derivatives), to counteract an abnormal synthesis of collagen and its accumulation in the tissues. This particular property could be linked to a structural analogy with a natural dipeptide, L-glycyl-L-proline that favours the collagen degradation, but also to their antioxidative properties because the oxidative stress has recently been implicated in the collagen overproduction (J. C. Geesin, L. J. Hendricks, P. A. Falkenstein, J. S. Gordon, R. A. Berg "Regulation of collagen synthesis by ascorbic acid: Characterization of the role of ascorbate—stimulated lipid peroxidation" Archives of Biochemistry and Biophysics, vol. 290, no 1 (1991) P. 127–132).

The accumulation of collagen in the heart tissue is one of the major complications of diabetes.

This type of compounds is indicated in order to reduce the cheloids associated with a collagen overproduction at the time of the healing process. As far as the pseudodipeptides according to the invention can also behave as anti-histaminic and that it has been recently proved that histamine stimulates the collagen production (A. Hatamochi, H. Ueki, C. Mauch, T. Krieg "Effect of histamine on collagen and collagen m-RNA production in human skin fibroplast", Journal of Dermatologic Sciences, Vol 2 (1991), P. 401–412), potptoides according to the invention are more especially adapted to this application.

Applications as Stabilizer and Preservative

The excellent tolerance, towards pseudodipeptides according to the invention, and their moderated antioxidant and cytostimulating properties allow to propose these products for the preservation and the protection of substance sensitive to oxidation, of food processing or organs and tissues preserved ex-vivo.

We can quote the prevention of oxidation of liposomes in order to improve their stability and avoid the formation of toxic by-products, the protection of hyaluronic acid blended in cosmetic formula against the depolymerisation action of free radicals, and the protection of oils and food products sensitive to oxidation, and diet products.

The products of the invention allow one to improve the preservation of blood and serum vaccine, the protection of organs dedicated to transplantation (in particular for heart transplant).

What is claimed is:

1. Chemical process for the preparation of the product of the formula:

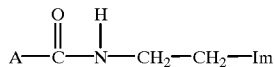

in which

A is:

a)

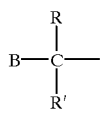

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N═C(—Y)—Y' in which Y is hydrocarbon and Y' is hydrogen or hydrocarbon; or

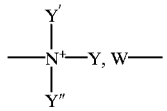

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

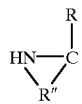

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole comprising the following steps:
N-protecting said alpha aminoacid by a group X,
O-activating said alpha aminoacid by a group Y,
Coupling said N-protected and O-activated alpha amino acid with histamine or methyl-substituted histamine.

2. Process according to the claim 1 wherein the alpha aminoacid is O-activated by esterification of the carboxylic acid function of said aminoacid.

3. Process according to the claim 2 wherein the esterification step comprises a reaction with a compound selected from the group consisting of: cyanomethyl alcohol, o-nitrophenol, 2,4,5-trihlorophenol, p-nitrophenol, 2,4-dinitrophenol, pentachlorophenol, pentafluorophenol, N-hydroxyphtalamide, -hydroxysuccinimide, 1-hydroxypiperidine and 5-chloro-8-hydroxyquinoline.

4. Enzymatic process for the preparation of the product of the formula:

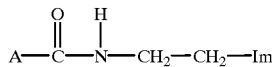

in which

A is:

a)

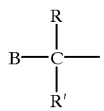

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N═C(—Y)—Y' in which Y is hydrocarbon and Y' is hydrogen or hydrocarbon; or

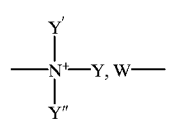

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

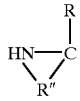

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole wherein an alpha aminoacid reacted is with histamine or methyl-substituted histamine in the presence of hydrolase enzymatic catalyst.

5. Process according to the claim 4 wherein said enzymatic catalyst is hydrolase selected from the group consisting of lipases extracted from micro-organisms or from animal origin, and proteases.

6. A medicine for treatment of cataracts comprising a cataract treatment effective amount of an active ingredient and a carrier therefor, wherein the active ingredient comprises the pseudodipeptide compound of the formula:

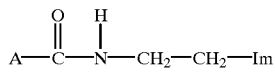

in which

A is:
a)

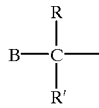

in which

B is primary amine; secondary amine of the formula —NH—X in which X is hydrocarbon, fluoroalkyl, acyl or amine; cycloalkyl or lactam tertiary cyclic amine: —N(—Y)—Y' in which Y and Y' are hydrocarbon, acyl or acyloxy; —N=C(—Y)—Y' in which Y is hydrocarbon and Y' is hydrogen or hydrocarbon; or

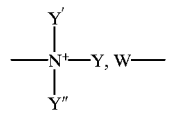

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

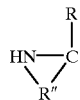

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

7. A medicine for treatment of atherosclerosis comprising atherosclerosis effective amount of an active ingredient and a carrier therefor, wherein the active ingredient comprises the pseudodipeptide compound of of the formula:

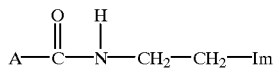

in which

A is:
a)

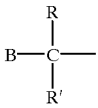

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

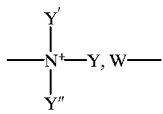

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

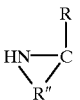

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

8. A medicine for treatment of inflammation comprising an anti-inflammatory effective amount of an active ingredient and a carrier therefor, wherein the active ingredient comprises the pseudodipeptide compound of the formula:

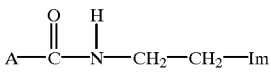

in which

A is:
a)

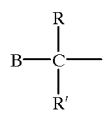

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

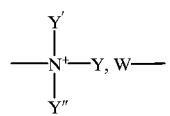

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or
b)

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

9. A medicine for treatment of oxidative stress skin disease comprising antioxidative stress skin disease effective amount of an active ingredient and a carrier therefor, wherein the active ingredient comprises the pseudodipeptide compound of the formula:

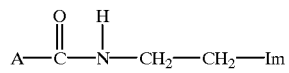

in which

A is:
a)

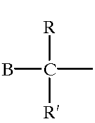

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

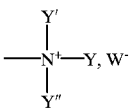

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or

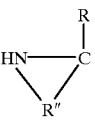

in which

R is hydrogen, fluorine, fluoroalkyl, acyl or hydrocarbon unsubstituted or substituted by one or more said functional groups and R' is acyl or hydrocarbon optionally substituted by one or more said functional groups, and Im is an imidazole or N-substituted imidazole.

10. A medicine for treatment of vascular disease comprising a vascular disease effective amount of an active ingredient and a carrier therefor, wherein the active ingredient comprises the pseudodipeptide compound of the formula:

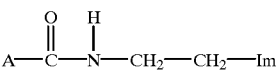

in which

A is:

a)

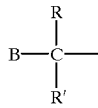

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

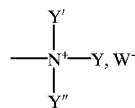

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

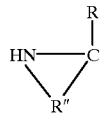

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

11. A medicine for promoting tissue healing comprising a tissue healing effective amount of an active ingredient and a carrier therefor, wherein the active ingredient comprises the pseudodipeptide compound of the formula:

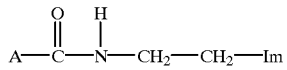

in which

A is:

a)

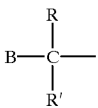

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

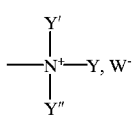

in which Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

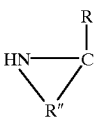

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

12. A medicine for gastric lesion comprising a gastric lesion effective amount of an active ingredient and a carrier therefor, wherein the active ingredient comprises the pseudodipeptide compound of the formula:

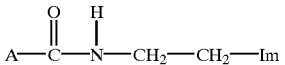

in which

A is:
a)

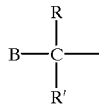

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

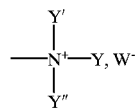

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or
b)

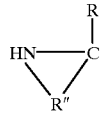

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

13. A radioprotective medicine comprising a radio- protective effective amount of an active ingredient and a carrier therefor, wherein the active ingredient comprises the pseudodipeptide compound of the formula:

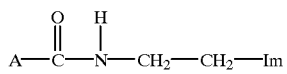

in which

A is:
a)

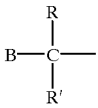

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

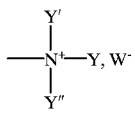

in which

Y, Y' and Y' are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or
b)

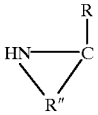

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

14. A collagen inhibitor medication comprising a collagen inhibitor effective amount of an active ingredient and a carrier therefor, wherein the active ingredient comprises the pseudodipeptide compound of the formula:

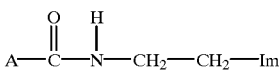

in which

A is:

a)

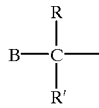

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

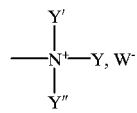

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

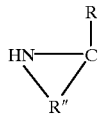

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

15. A medicine for treatment of diabetes complications comprising an effective amount of an active ingredient and a carrier therefor, wherein the active ingredient comprises the pseudodipeptide compound of the formula:

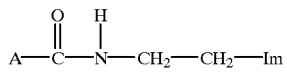

in which

A is:

a)

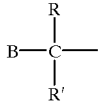

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

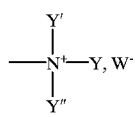

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

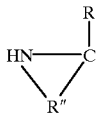

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

16. A medicine for immunostimulation of vaccines comprising an immunostimulator effective amount of an active ingredient and a carrier therefor, wherein the active ingredient comprises the pseudodipeptide compound of the formula:

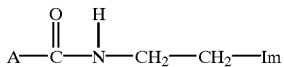

in which

A is:

a)

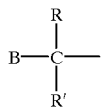

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

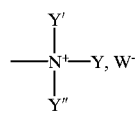

in which Y, Y' and Y'' are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

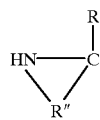

in which

R is hydrogen, fluorine, fluoroalkyl, acyl or hydrocarbon unsubstituted or substituted by one or more said functional groups and R'' is acyl or hydrocarbon optionally substituted by one or more said functional groups, and Im is an imidazole or N-substituted imidazole.

17. An anti-platelet aggregation medicine comprising an anti-platelet aggregation effective amount of an active ingredient and a carrier therefor, wherein the active ingredient comprises the pseudodipeptide compound of the formula:

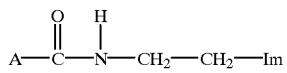

in which

A is:

a)

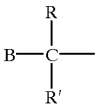

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

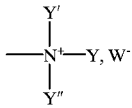

in which

Y, Y' and Y'' are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

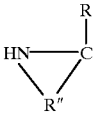

in which

R is hydrogen, fluorine, fluoroalkyl, acyl or hydrocarbon unsubstituted or substituted by one or more said functional groups and R'' is acyl or hydrocarbon optionally substituted by one or more said functional groups, and Im is an imidazole or N-substituted imidazole.

18. A medicine for treatment of allergy comprising an anti-allergy effective amount of an active ingredient and a carrier therefor, wherein the active ingredient comprises the pseudodipeptide compound of the formula:

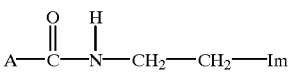

in which

A is:
a)

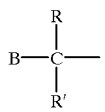

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

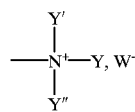

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyle, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or
b)

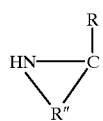

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

19. A composition for the regeneration and rejuvenation of tissues comprising an effective regeneration and rejuvenation amount of an active agent and a carrier therefor, wherein the active ingredient comprises the pseudodipeptide compound of the formula:

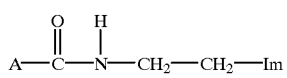

in which

A is:
a)

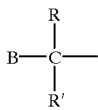

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

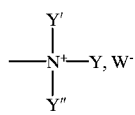

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or
b)

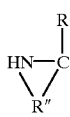

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

20. A composition comprising a food, organ or ex vivo tissue in combination with an anti-oxidant, and the pseudodipeptide compound of the formula:

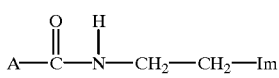

in which

A is:

a)

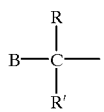

in which

B is primary amine; secondary amine of the formula —NH—X in which X is hydrocarbon, fluoroalkyl, acyl or amine; cycloalkyl or lactam tertiary cyclic amine; —N(—Y)—Y' in which Y and Y' are hydrocarbon, acyl or acyloxy; —N=C(—Y)—Y' in which Y is hydrocarbon and Y' is hydrogen or hydrocarbon; or

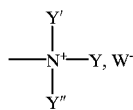

in which

Y, Y' and Y" are hydrocarbon and the counter ion W is halide, sulfate, phosphate, bicarbonate, para-toluene sulfonate or a carboxylic acid-containing radical, R is fluorine, fluoroalkyl, a functional group selected from the group consisting of sulfate, phosphate and carboxylic acid, acyl, linear $C_{2-6}$ alkyl unsubstituted or substituted by one or more said functional groups, alkenyl or aryl optionally substituted by one or more said functional groups, and R' is hydrogen, fluorine, alkyl or fluoroalkyl; or b)

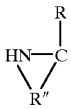

in which

R is hydrogen, fluorine, fluoroalkyl, acyl or hydrocarbon unsubstituted or substituted by one or more said functional groups and R" is acyl or hydrocarbon optionally substituted by one or more said functional groups, and Im is an imidazole or N-substituted imidazole.

* * * * *